United States Patent [19]

Alspector

[11] Patent Number: 4,824,560

[45] Date of Patent: Apr. 25, 1989

[54] SEPARATION OF MATERIALS FROM A LIQUID DISPERSION BY SEDIMENTATION

[75] Inventor: Benjamin Alspector, Jerusalem, Israel

[73] Assignee: Assaf Pharmaceutical Industries Ltd., Israel

[21] Appl. No.: 848,133

[22] Filed: Apr. 4, 1986

[30] Foreign Application Priority Data

Apr. 18, 1985 [IL] Israel ................................. 74967

[51] Int. Cl.⁴ .............................................. B01D 43/00
[52] U.S. Cl. ................................. 209/208; 210/512.1; 210/789; 422/102; 494/16; 494/37
[58] Field of Search ............... 209/148, 199, 451, 208, 209/209; 494/16, 20, 37; 210/514–516, 518, 789, 512.1; 422/101, 102, 72; 436/177; 604/191, 403; 206/219; 215/6

[56] References Cited

U.S. PATENT DOCUMENTS

| | | | |
|---|---|---|---|
| 1,457,560 | 6/1923 | Tuber | 209/199 |
| 1,530,758 | 3/1972 | Coleman | 209/199 X |
| 1,530,759 | 3/1975 | Coleman | 209/199 X |
| 2,110,237 | 3/1938 | Parsons | 422/102 X |
| 2,170,411 | 8/1939 | Jacobs et al. | 210/515 X |
| 2,587,012 | 2/1952 | Tuggle | 209/199 |
| 2,700,467 | 1/1955 | Dorman | 209/199 |
| 2,779,472 | 1/1957 | Febbraro | 210/514 |
| 3,300,051 | 1/1967 | Mitchell | 494/16 X |
| 3,513,976 | 5/1970 | James | 210/782 |
| 3,647,070 | 3/1972 | Adler | 210/516 X |
| 3,654,925 | 4/1972 | Holderith | 210/789 X |
| 3,750,645 | 8/1973 | Bennett et al. | 422/101 X |
| 3,849,072 | 11/1974 | Ayres | 494/16 X |
| 3,879,295 | 4/1975 | Glover et al. | 210/789 X |
| 3,965,889 | 6/1976 | Sachs | 210/789 X |
| 4,066,414 | 1/1978 | Selby | 422/102 |
| 4,134,832 | 1/1979 | Heimreid | 494/16 X |
| 4,147,628 | 4/1979 | Bennett et al. | 210/789 |
| 4,154,690 | 5/1979 | Ballies | 494/16 X |
| 4,350,593 | 9/1982 | Kessler | 494/16 X |
| 4,511,349 | 4/1985 | Nielsen et al. | 494/16 |
| 4,533,468 | 8/1985 | Ensor et al. | 209/199 X |

Primary Examiner—James B. Marbert
Assistant Examiner—Edward M. Wacyra
Attorney, Agent, or Firm—Steinberg & Raskin

[57] ABSTRACT

Sedimentation classification of particulate material in liquid dispersion. The dispersion is centrifuged in a tubular vessel comprising at least two neighboring compartments communicating via at least one opening which may be capillary. The lowermost compartment has a sealed bottom and the uppermost has an open upper end. Upon completion of the centrifugation a liquid fraction with dispersed particulate material is decanted from the uppermost compartment. Useful products may also be recovered from other compartments.

21 Claims, 3 Drawing Sheets

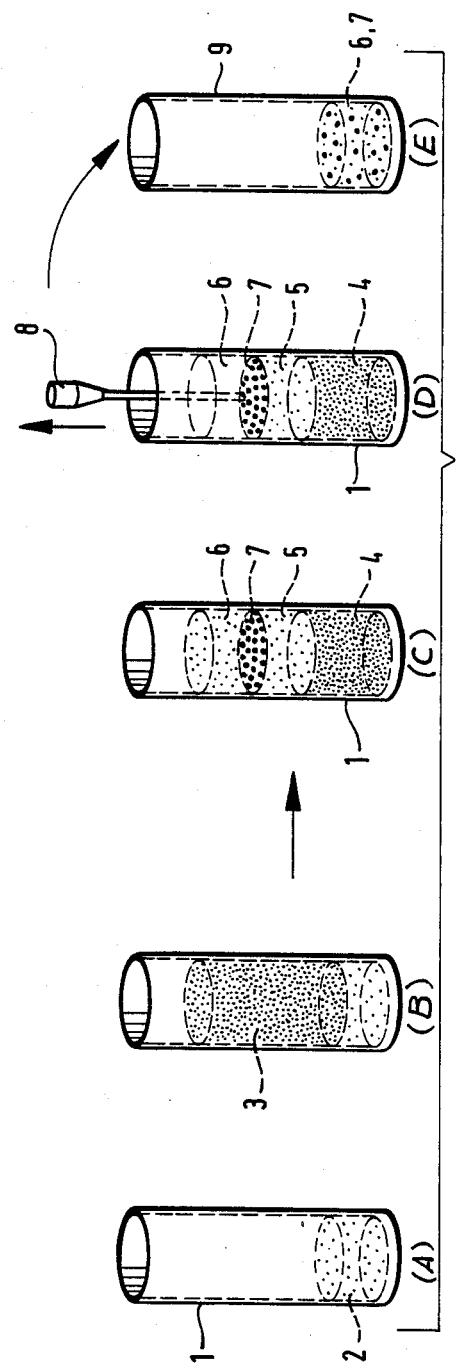
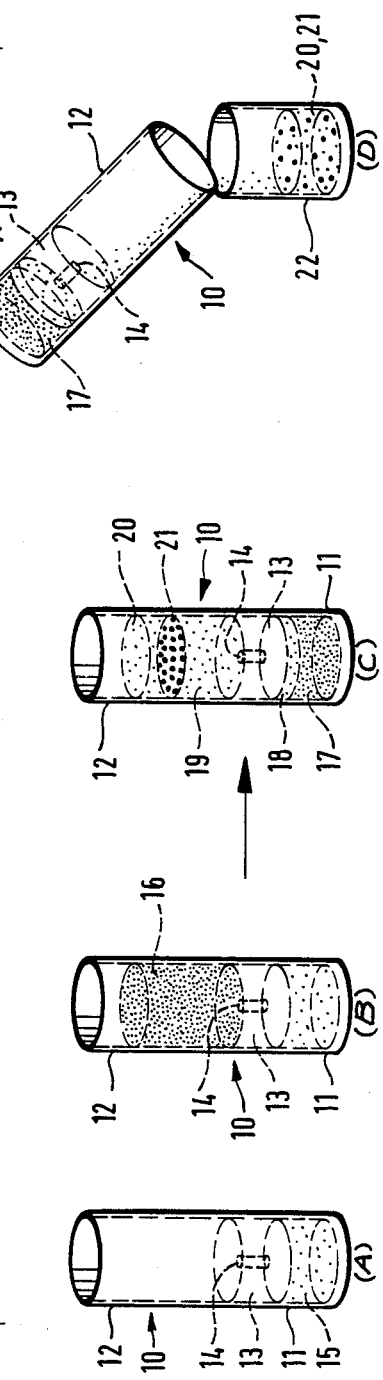
Fig. 1 PRIOR ART
Fig. 2

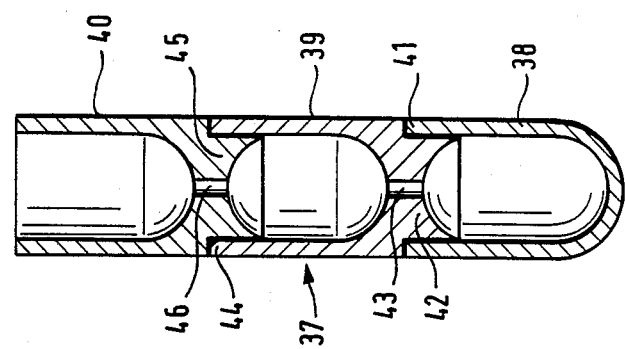
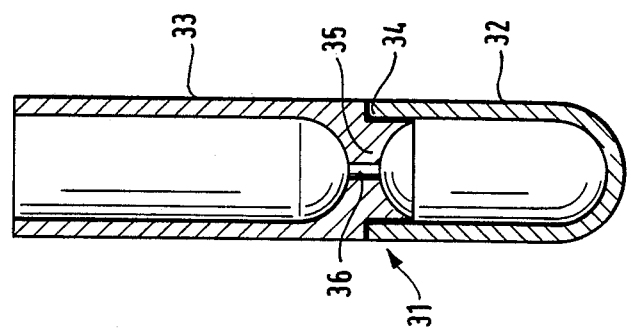
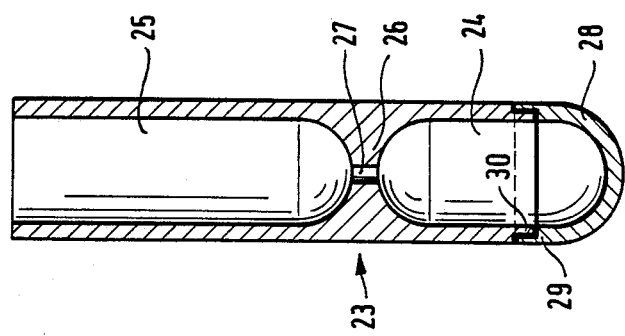

SEPARATION OF MATERIALS FROM A LIQUID DISPERSION BY SEDIMENTATION

BACKGROUND OF THE INVENTION

The present invention concerns classification of particulate material in liquid dispersion by sedimentation so as to obtain at least two fractions of particulate material of different densities, and the recovery of at least one of such fractions. The sedimentation may be induced by gravity by centrifugation and the liquid dispersion to be classified in accordance with the present invention may be suspensions or emulsions.

The present invention is applicable to a variety of purposes such as diagnostic, analytical and preparative operations, typical applications being the separation of leucocytes from native blood, the splitting of a recovered leucocyte fraction into B-cells and T-cells, separation of an antigen/antibody complex produced in vitro in a reaction mixture from other particulate material, classification of lipoproteins, classification of marrow cells and the like.

For certain centrifugation techniques there are commonly used test tube-like vessels so designed that they are capable of withstanding the high stresses prevailing during centrifugation. In such a vessel the interface between layers resulting from centrifugation is a labile structure and consequently special care has to be taken in order to avoid back-mixing of the fractions. This in turn gives rise to problems in the separation of fractions from each other with the consequence that such separation is a tedious and slow operation.

SUMMARY OF THE INVENTION

It is accordingly the object of the present invention to provide an improved method and means for the classification of particulate material in liquid dispersion free of the shortcomings of the prior art.

In accordance with the present invention there is provided a method of classification by sedimentation of a particulate material in liquid dispersion, characterized by:

(i) providing a tubular vessel comprising at least two aligned compartments with each two neighbouring compartments communicating via at least one opening and having a first extreme compartment with a sealed bottom and a second extreme compartment with an open upper end;

(ii) charging said liquid dispersion into said vessel;

(iii) subjecting the so charged vessel to centrifugation; and (iv) decanting a liquid fraction with particulate material dispersed therein from said second extreme compartment.

The opening may be in the form of a bore or hole or a plurality of bores and/or holes and the diameter thereof is not critical and will depend, inter alia, on the length of the hole/s or bore(s) and the nature of the particulate material to be classified. It is preferred that the diameter should not exceed 10 mm and particularly preferred are openings having a diameter of not more than 5 mm., and the openings may be considerably narrower, e.g. of a capillary nature.

During decantation of the liquid from the second extreme compartment, the entire vessel may be inverted without any danger of back-mixing.

The method according to the invention may be performed by gravity sedimentation or by centrifugation induced sedimentation.

If desired the method according to the invention may be performed with density adjustment prior to centrifugation, as known per se, e.g. by the addition of a solute or of a working liquid of preselected density. Where a working fluid is used it may be of a uniform density intermediary between the densities of particulate material fractions to be classified, or have a density gradient also as known per se.

Where, in accordance with the invention only two particulate fractions are to be separated from each other and only the lighter fraction is to be recovered as, for example, in many instances of blood diagnosis where only the leucocytes, which are the lighter fraction, have to be recovered, the vessel may be made as one disposable unit comprising only two compartments and be discarded after the recovery of the upper fraction as specified. Where, on the other hand, the dispersed particulate material is to be fractionated into two or more fractions of different densities, each of which is to be recovered separately, the vessel is so designed that upon centrifugation the contents of each compartment may be recovered separately. When the vessel comprises only two compartments the bottom portion of the first extreme compartment may be removable and upon completion of centrifugation the contents of the second extreme compartment are recovered by decantation as specified, and the contents in the first extreme compartment are recovered by removal of the bottom part and drainage.

Alternatively and where the dispersed particulate material is to be classified into more than two fractions and the vessel comprises accordingly more than two compartments, the vessel may be in the form of a disassemblable unit comprising two or more constituent parts each of which corresponds to one compartment, and upon completion of the centrifugation operation the vessel is disassembled and the contents of each compartment are recovered separately.

The invention further comprises a tubular sedimentation vessel for carrying out the above method comprising at least two aligned compartments with each two neighbouring compartments communicating via at least one opening, having a first extreme compartment with a sealed bottom and a second extreme compartment with an open end.

It is preferred that the diameter of the openings should not exceed 10 mm and particularly preferred are vessels as specified in which the diameter of the openings does not exceed 5 mm.

In accordance with one embodiment of a vessel according to the invention, the vessel is in form of a disposable unit having two compartments.

In accordance with another embodiment of a vessel according to the invention, the bottom of the first extreme compartment is sealed by means of a removable bottom piece.

In accordance with yet another embodiment of a vessel according to the invention, the vessel is disassemblable and comprises tubular constituent parts, each corresponding to one compartment of the assembled vessel, each two neighbouring parts being adapted for tight interengagement in that a downward protecting stud portion of one unit is adapted to be received in a tight fit by an open end of the other unit.

The openings through which two neighbouring units in a vessel according to the invention communicate with each other may be provided by a bored partition by which two neighbouring compartments are separated from each other. Alternatively, it is also possible to use porous material.

In the following description the invention is described with reference to centrifugation induced sedimentation, it being understood that it is not limited thereto and applies also to gravity sedimentation.

BRIEF DESCRIPTION OF THE DRAWINGS

The invention is illustrated, by way of example only, in the accompanying drawings in which:

FIGS. 1 (A)–(E) shows a prior art centrifugation separation scheme;

FIGS. 2 (A)–(D) shows a centrifugation separation scheme according to the invention; and FIGS. 3–6 show various embodiments of centrifugation vessels according to the invention.

DESCRIPTION OF THE PRIOR ART

Figure 3:
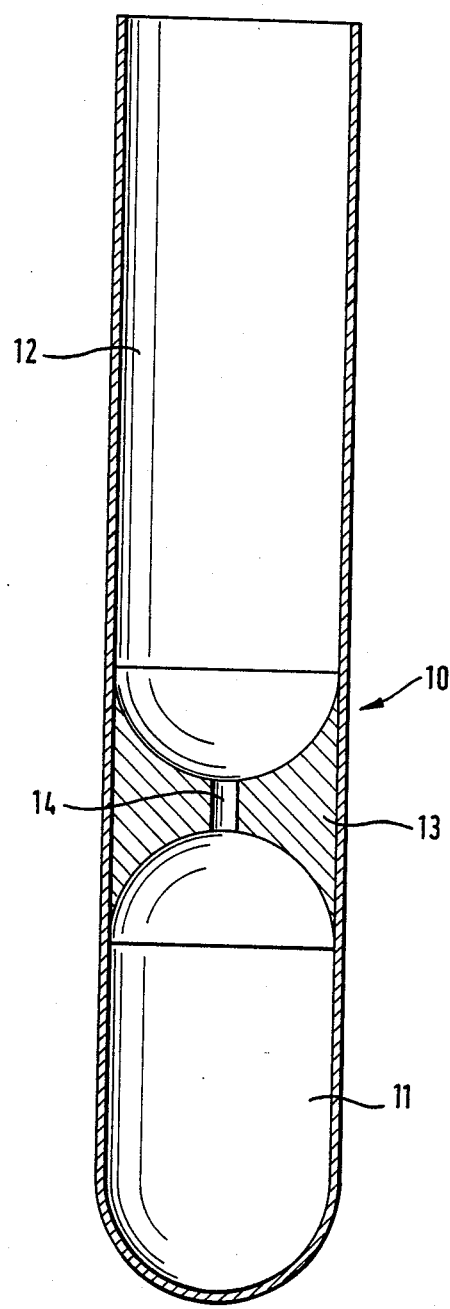

The prior art centrifugation separation scheme shown in FIG. 1 concerns the classification of blood for the separation of leucocytes and erythrocytes from each other and the recovery of the leucocytes.

As shown, a centrifugation tube 1 is charged with a polysaccharide solution 2 which serves for density adjustment, and a blood portion 3 is then charged on top of the polysaccharide solution 2. During charging care has to be taken that the blood 3 and the polysaccharide solution 2 remain stratified without any undue mixing which might affect the classification efficiency. Upon centrifugation the material inside vessel 1 becomes stratified with the formation of a lower clot 4 of erythrocytes, an intermediary body of liquid 5 consisting of polysaccharide solution and an upper body of liquid 6 consisting mainly of plasma with an agglomerate of leucocytes 7 floating near the interface with body 5. For the recovery of the leucocytes 7 the upper liquid body 6 has to be sucked out very carefully by means of a pipette 8 and transferred into a different vessel 9. The suction operation has to be done very carefully in order to avoid back-mixing with the erythrocytes in clot 4. Because of this, the separation of the upper liquid body 6, 7 is a tedious operation and cannot be carried out to completion.

DESCRIPTION OF THE PREFERRED EMBODIMENTS

The centrifugation separation according to the invention shown diagrammatically in FIG. 2, also concerns the classification of blood into leucocytes and erythrocytes with the aid of density adjustment by means of a polysaccharide solution. As shown, tubular vessel 10 comprising a lower compartment 11 and an upper compartment 12 separated from each other by a partition in form of a double concave block 13 with a central capillary bore 14, is charged with a polysaccharide solution 15 such that the solution reaches the upper end of the capillary bore 14. Thereafter the vessel 10 is charged with a blood portion 16 which is poured into the upper compartment 12. No special care has to be taken during this charging operation because block 13 with the capillary bore 14 prevent any significant mixing of the body of solution 15 and the blood portion 16. Upon centrifugation the material inside vessel 10 stratifies into a lowermost erythrocyte clot 17 with a small body 18 of polysaccharide solution on top, an intermediary body 19 of polysaccharide solution, an upper body 20 of plasma with an agglomerate of leucocytes 21 floating therein near the interface with body 19. For the recovery of the leucocytes 21 the entire contents of the upper compartment 12 is poured into another vessel 22 by decantation as shown on the righthand side of FIG. 2. During this decantation the capillary bore 14 ensures that none of the clot of erythrocytes 17 escapes from compartment 11 whereby any back-mixing of the erythrocytes and leucocytes is prevented.

It is assumed that the erythrocytes are not required in this particular operation and consequently the vessel 10 is designed as a disposable unit which is discarded after the contents of the upper compartment 12 has been poured into vessel 22 as specified.

The sedimentation vessel according to the invention used in the centrifugation separation scheme according to FIG. 2 is shown once more in FIG. 3 where the same numerals are used as in FIG. 2. As shown, vessel 10 comprises a lower compartment 11 and an upper compartment 12 separated from each other by a double concave block 13 having a central capillary bore 14 through which compartments 11 and 12 communicate with each other. The diameter of bore 14 may not exceed 5 mm while the length thereof is not critical. The double concave design of block 13 ensures that no air pockets are formed in the lower compartment 11 and that a sump is formed in the upper compartment 12 for the complete drainage during centrifugation of the denser fraction to bore 14. The vessel of FIG. 3 is designed to be disposable.

The embodiment of the vessel according to the invention shown in FIG. 4 is designed for repeated use and it enables the separate recovery of both the upper and lower fractions. As shown, the vessel 23 is essentially of a design similar to that of FIG. 3. It comprises a lower compartment 24 and an upper compartment 25 separated from each other by a partition in form of a double concave block 26 having a central capillary bore 27.

The lower compartment 24 is formed with a removable bottom piece 28 having a circumferential recess 29 adapted to receive in a tight fit a downwardly projecting stud portion 30 of the main body of vessel 23.

The embodiment of FIG. 4 is used where two sedimentation fractions are each to be recovered. Accordingly, after centrifugation the contents of the upper compartment 25 are withdrawn by decantation similarly as shown in FIG. 2 and thereafter the bottom piece 28 is removed whereupon the contents of the lower compartment 24 are drained off.

The embodiment of FIG. 5 is again designed for repeated use and it comprises two constituent parts, each corresponding to one compartment of the vessel. As shown the vessel 31 comprises a lower unit 32 and an upper unit 33. The lower unit 32 has an upper, open end portion 34 while the upper unit 33 has a downwardly projecting stud portion 35 fitted with a capillary bore 36 and adapted to be received in a tight fit by the upper end portion 34 of the lower unit 32. Stud portion 35 also forms the block that separates units 32 and 33 from each other and similar as in the embodiment of FIG. 4 it is of a double concave shape.

The embodiment of FIG. 5 is also used where two fractions are each to be recovered. Accordingly after centrifugation the contents of the upper unit 33 are removed by decantation in a similar way as shown in FIG. 2. When this decantation is complete the upper unit 33 is removed whereby the fraction that has collected in the lower chamber 32 becomes accessible.

The embodiment of the centifugation vessel 37 shown in FIG. 6 comprises three constituent units 38, 39 and 40. The lowermost unit 38 is of a similar design as unit 32 in FIG. 5 and it comprises an upper, open end portion 41. The intermediary unit 39 comprises a downward projecting stud portion 42 having a central capillary bore 43 of double concave shape similar as stud 35 of FIG. 5. The intermediary unit 39 further comprises an upper open end portion 44 and the upper unit 40 comprises a downward projecting double concave stud portion 45 fitted with a central, capillary bore 46.

In the assembled state the stud portion 42 of the intermediary unit 39 is received in a tight fit by the open end portion 41 of the lower unit 38 and likewise the downward projecting stud portion 45 of the uppermost unit 40 is received in a tight fit by the open end portion 44 of the intermediary unit 39.

The embodiment of FIG. 6 is used for the separate recovery of three fractions: After separation of the uppermost fraction in unit 40 by decantation, unit 40 is removed and the intermediary fraction that has collected in unit 39 is separated again by decantation, whereupon that unit is also removed leaving the third, lowermost fraction accessible in unit 38.

WORKING EXAMPLES

EXAMPLE 1

Separation of Mononuclear Cells from Blood 1.3 mm of an aqueous polysaccharide solution (d=1.077) available under the trade mark Histopaque from Sigma Chemical Co. of St. Louis, Mo., U.S.A. are poured into the lower compartment 11 of a vessel according to FIG. 3 so that the upper meniscus of the liquid is at the top of the bore 14. 2.0 ml blood are poured into the upper chamber of the vessel without any special precaution being required to avoid mixing of the blood with the polysaccharide solution, such mixing being essentially prevented by the special design of the vessel. The vessel with its contents is then centrifuged at 750 xg for a period of 20 minutes. After centrifugation the upper compartment 12 contains three layers, an upper layer of plasma, a white interface layer containing the mono-nuclear cells and a lower layer containing the said polysaccharide solution. The lower compartment 11 contains a layer of the polysaccharide solution and at the bottom a clot of red blood cells. The entire contents of the upper compartment 12 are poured into another vessel with no special precautions being required, any such backmixing being prevented automatically by block 13 and capillary bore 14. Phosphate buffer solution (PBS) is added to the mononuclear cell suspension recovered from the upper compartment 12 and that suspension is then processed as may be required.

EXAMPLE 2

Demonstration of Improved Separation Efficiency

The improvement of the efficiency of separation in accordance with the invention was demonstrated as follows: 59 samples of blood were processed in parallel using respectively the prior art method as illustrated in FIG. 1 and the method according to the invention as illustrated in FIG. 2 and described in Example 1. Protein content of the resultant mononuclear cell suspension was assayed according to the method of Lowry.

The results of this comparative study are summarized in the table below:

| Method | Number of Samples | Yield* | Efficiency factor |
|---|---|---|---|
| Prior art method | 59 | 0.297 | 1.00** |
| Method according to the invention | 59 | 0.367 | 1.24 |

*mg protein in mononuclear cell suspension derived from 1.0 ml blood (mean).
**By definition.

The advantages which are obtainable in accordance with the invention as compared to the prior art may be summed up briefly as follows:

(i) Charging in case of density adjustment by means of solutions: whereas in accordance with the prior art charging must be effected very carefully in order to avoid initial mixing of the sample with the density adjustment solution, in accordance with the invention such mixing is essentially prevented and accordingly no precaution has to be taken during sampling.

(ii) Removal of an upper fraction: whereas in accordance with the prior art upon sedimentation an upper fraction can be removed only by suction and special care has to be taken to avoid any back-mixing, in accordance with the invention an upper fraction is poured out of the upper compartment by decantation and any back-mixing is inherently prevented;

(iii) Handling of vessel after sedimentation: whereas in accordance with the prior art handling of the sedimentation tube after sedimentation is restricted and should be done only with the greatest care, there are no limitations on the handling of the sedimentation vessel in accordance with the present invention.

(iv) Simultaneous operation: whereas in accordance with the prior art one operator can only handle one sedimentation tube at a time with the consequence that recovery of upper fractions from a plurality of sedimentation tubes can only be effected sequentially, in accordance with the invention a plurality of sedimentation vessels can be handled simultaneously, e.g. by placing them in a rack and inverting the rack so as to pour out simultaneously the contents of all the upper compartments.

(v) Efficiency: whereas in accordance with the prior art the recovery yields of upper fractions are inherently incomplete because of the danger of backmixing during suction, in accordance with the present invention an upper fraction can be recovered in toto without any danger of back-mixing whereby the separation efficiency is increased by 20–25%.

I claim:

1. A method of classification by centrifugation of particulate material in liquid dispersion with at least two fractions, characterized by:
   (i) providing a tubular vessel comprising at least two aligned coaxial compartments with each two neighbouring compartments communicating via at least one opening, said tubular vessel having a first extreme compartment with a sealed bottom and a second extreme compartment with an open end;
   (ii) charging a working liquid into said tubular vessel via said second extreme compartment thereof so as to fill completely said first extreme compartment, said working liquid having a density intermediate the densities of said at least two particulate material fractions to be classified;

(iii) charging said particulate material in liquid dispersion into said vessel via said second extreme compartment;

(iv) subjecting the so-charged vessel to centrifugation, thereby to cause a heaviest fraction of said particulate material to migrate axially into said first extreme compartment; and (v) decanting a liquid fraction with particulate material dispersed therein from said second extreme compartment.

2. A method according to claim 1 wherein said working liquid has a density gradient.

3. A method according to claim 1 comprising using a vessel with only two compartments, after sedimentation recovering only the contents of the second extreme compartment and then discarding said vessel.

4. A method according to claim 1 comprising using a vessel with only two compartments, so designed that said first extreme compartment is adapted for the recovery of its contents, and after sedimentation recovering the contents of each compartment.

5. A method according to claim 1 comprising using a disassemblable vessel with two or more compartments, disassembling the vessel after sedimentation and recovering the contents of each compartment.

6. The method of claim 1, wherein said working liquid is miscible with a liquid phase of said dispersion.

7. A tubular centrifugation vessel for carrying out a method of classifying by centrifugation a particulate material in liquid dispersion, comprising
at least two axially-aligned compartments with each two neighbouring compartments communicating via at least one opening,
said tubular centrifugation vessel having a first extreme compartment with a sealed bottom and a second extreme compartment with an open end,
said at least one opening being of a size to admit in the course of centrifugation the passage of a fraction of the particulate material in liquid dispersion that is being centrifuged, and not admitting passage of the particulate material in liquid dispersion under normal gravitational conditions when a working liquid is charged to a level of said at least one opening, thereby forming a meniscus.

8. A vessel according to claim 7 having two compartments.

9. A vessel according to claim 8 having a removable bottom.

10. A vessel according to claim 7 being disassemblable and comprising tubular constituent parts, each corresponding to one compartment of the assembled vessel, each two neighbouring parts being adapted for tight interengagement in that a downwardly projecting stud portion of one unit is adapted to be received in a tight fit by an open end of the other unit.

11. A vessel according to claim 7 comprising a partition between every two neighbouring compartments, having at least one opening.

12. A vessel according to claim 7 wherein the diameter of any opening does not exceed 10 mm.

13. A vessel according to claim 12 wherein the diameter of any opening does not exceed 5 mm.

14. A vessel according to claim 7 wherein the opening is of a capillary nature.

15. A vessel according to claim 7 wherein every two compartments are separated by porous material.

16. The tubular vessel of claim 7, additionally comprising
a partition situated in said vessel and separating each compartment from the other compartment, and
said at least one opening being a capillary bore extending through said partition.

17. The combination of claim 16, wherein said partition is in the form of a double concave block.

18. The combination of claim 16, additionally comprising
a removable bottom piece enclosing at least a part of said first compartment, whereby contents of the same can be drained off.

19. The combination of claim 18, wherein said bottom piece comprises a circumferential recess and a remainder of said vessel comprises a projecting stud,
with said stud and recess formed to engage in a tight fit.

20. The combination of claim 18, wherein
said removable bottom piece comprises an open upper end, and said partition comprises a projecting stud portion,
with said stud portion and upper end of said bottom piece formed to engage in a tight fit.

21. The combination of claim 20, additionally comprising
a third compartment aligned with said first two compartments,
a second partition situated to separate said second and third components, and
a second capillary bore extending through said second partition and through which said second and third compartments communicate,
wherein said second partition comprises a projecting stud portion formed to engage said open end of said second compartment in a tight fit, and said second and third compartments are separable from one another.

* * * * *